(12) United States Patent
Takahashi et al.

(10) Patent No.: US 7,008,379 B2
(45) Date of Patent: Mar. 7, 2006

(54) NONINVASIVE SPHYGMOMANOMETER

(75) Inventors: Yukio Takahashi, Komochi-mura (JP); Eikichi Suda, Komochi-mura (JP)

(73) Assignee: Nihon Seimitsu Sokki Co., Ltd., Gunma (JP)

( * ) Notice: Subject to any disclaimer, the term of this patent is extended or adjusted under 35 U.S.C. 154(b) by 0 days.

(21) Appl. No.: 10/682,816

(22) Filed: Oct. 10, 2003

(65) Prior Publication Data

US 2004/0127801 A1    Jul. 1, 2004

(30) Foreign Application Priority Data

Nov. 8, 2002  (JP) .............................. 2002-324867

(51) Int. Cl.
*A61B 5/02* (2006.01)
*A61B 5/103* (2006.01)
*A61B 5/117* (2006.01)

(52) U.S. Cl. ...................... 600/490; 600/587
(58) Field of Classification Search ........ 600/490–499, 600/481, 485, 587
See application file for complete search history.

(56) References Cited

U.S. PATENT DOCUMENTS

| | | | |
|---|---|---|---|
| 3,812,844 A * | 5/1974 | Sokol ......................... | 600/499 |
| 4,429,699 A * | 2/1984 | Hatschek .................... | 600/494 |
| 4,501,280 A * | 2/1985 | Hood, Jr. .................... | 600/490 |
| 5,595,180 A * | 1/1997 | Ogura et al. ................ | 600/499 |
| 6,228,035 B1 * | 5/2001 | Packman et al. ........... | 600/485 |
| 2003/0040700 A1 * | 2/2003 | Hickle et al. ................ | 604/67 |

FOREIGN PATENT DOCUMENTS

| | | |
|---|---|---|
| JP | 62-152702 | 9/1987 |
| JP | 6-245911 | 9/1994 |

* cited by examiner

*Primary Examiner*—Max F. Hindenburg
*Assistant Examiner*—Navin Natnithithadha
(74) *Attorney, Agent, or Firm*—Venable LLP; Catherine M. Voorhees

(57) ABSTRACT

A noninvasive sphygmomanometer capable of obtaining an accurate blood pressure value is provided without complicating a structure and with little time-consuming work. A photointerrupter 31, a wave-shaping circuit 75, a rotation number counting circuit 77, and a discharge amount calculating circuit 78 which measure a discharge amount of a pressure pump 13, and an arm circumference length detecting circuit 79 which calculates an arm circumference length of a subject person based on a relationship between a pressure in a bladder 8 provided in an armband 9 and the measured discharge amount of the pressure pump 13 is provided. Then, a blood pressure value is corrected based on the calculated arm circumference length.

3 Claims, 10 Drawing Sheets

FIG. 11

| UPPER ARM CIRCUMFERENCE LENGTH  mm | MAXIMUM BLOOD PRESSURE  mmHg | UPPER ARM CIRCUMFERENCE LENGTH  mm | MINIMUM BLOOD PRESSURE  mmHg |
|---|---|---|---|
| 150~180 | +15 | 150~200 | 0 |
| 190~220 | +10 | 210~260 | −5 |
| 230~260 | +5 | 270~310 | −10 |
| 270~300 | 0 | 320~370 | −15 |
| 310~340 | −5 | 380~430 | −20 |
| 350~380 | −10 | 440~470 | −25 |
| 390~410 | −15 | | |
| 420~490 | −25 | | |

( WHEN BLADDER OF 13 cm WIDE IS USED )

NONINVASIVE SPHYGMOMANOMETER

BACKGROUND OF THE INVENTION

1. Field of the Invention

The present invention relates to a noninvasive sphygmomanometer, and more particularly to the sphygmomanometer providing a function for correcting a measurement error according to a difference in arm circumference lengths of subject persons.

2. Description of the Related Art

Conventionally, the most general method for noninvasively measuring a blood pressure value is a method for interrupting bloodstream to peripheral regions by bringing pressure from outside to regions where arteries pass such as arms, wrists, or the like of a subject person and thereafter for observing Korotkoff sounds or a change of pulsation in the arteries during a process to gradually reduce the brought pressure, thereby measuring the blood pressure value.

Furthermore, to bring the pressure to the region where the arteries pass is conducted by winding an armband with a bladder as a bag to contain air therein on the region where the arteries pass and by applying and reducing pressure in the bladder from outside, and this controls interrupting and reopening the bloodstream to the peripheral regions.

However, this method is lower in measurement accuracy compared with an invasive method for directly measuring pressure in a blood vessel. The reason for this is that results of blood pressure measurement are different depending on an arm circumference length of the subject person or a size of the bladder for use. For example, when a width (a direction perpendicular to a direction of winding the armband) of the bladder is much shorter than the arm circumference length of the subject person, blood pressure is detected higher than an actual value; and reversely, when the width thereof is much longer, the blood pressure is detected lower than the actual value. Similarly, when a length (the direction of winding the armband) of the bladder is much shorter than the arm circumference length of the subject person, the blood pressure is detected higher than the actual value; and reversely, when the length thereof is much longer, the blood pressure is detected lower than the actual value. Therefore, it is ideal to prepare the bladders corresponding to all subject persons in order to obtain an accurate blood pressure value. However, it is difficult to actually commercialize and prepare them in a medical setting or the like if cost reduction, securement of space, needs of the accurate blood pressure value of the subject person, and the like are compared and considered.

Accordingly, considering a range of the arm circumference length where measurement errors are within a certain range as a range of a suitable arm circumference length of the bladder, plural armbands having different bladder sizes are often prepared in order to cover the range of the arm circumference length of the subject person which can be previously estimated. In actual measurement, the armband is selected by (1) measuring the arm circumference length of the subject person using a tape measure, or (2) by a hunch of a measuring person.

However, in the method (1), measurement with the tape measure is a time-consuming work; furthermore, there is a problem that the tape measure must be found out if the tape measure is not available at a site where measurement is taken place. Furthermore, in the method (2), there is a problem of an error in selection of the armband due to the hunch by the measuring person, resulting in lacking in accuracy.

Therefore, methods with accuracy and with little time-consuming work are disclosed. Specifically, (3) a method for marking the armband with a scale showing the arm circumference length (for example, refer to Utility Model 1), (4) a method for providing a display of a suitable range of the arm circumference length with the armband (for example, refer to Utility Model 1), (5) a method for providing a measurer of the arm circumference length with the armband, for example, an electric position detector such as a variable resistor or the like with the armband (for example, refer to Patent Document 2), and (6) a method for estimating the arm circumference length from a time required for applying pressure (for example, refer to Patent Document 2), specifically, a method for measuring the pressure in the bladder while applying pressure, and for estimating the arm circumference length of the subject person based on a time required for reaching a predetermined pressure value or a time required for reaching from the predetermined pressure value to a predetermined pressure value higher than therefrom, are disclosed.

[Patent Document 1]
Japanese Utility Model Laid-open No. Sho 62-152702 (FIG. 1 to FIG. 5)
[Patent Document 2]
Japanese Patent Laid-open No. Hei 6-245911 (Page 2, FIG. 2)

However, the aforementioned methods (3) to (6) have following problems.

In the method (3), whether or not a size of the bladder in the armband is appropriate for the subject person is determined from a scale value when the armband is wound on an arm of the subject person, and a correction of the blood pressure value to be measured is possible based on the scale value, and meanwhile, whether the bladder is appropriate or not is determined only after it is wound. Therefore, there is a problem that the bladder must be wound again in order to change the armband having a bladder of a different size if the bladder is not appropriate.

Furthermore, in order to take a measurement more accurately, a method for calculating the blood pressure value taking the measured arm circumference length into consideration is thought. However, in this case, there is a problem that the correction of the blood pressure value must be made by people, or that the arm circumference length must be directly inputted using an operation button of a sphygmomanometer.

In the method (4), as well as the method (3), there is a problem that the armband must be wound again because whether or not the bladder is appropriate is determined only after the armband is wound.

In the method (5), the accurate blood pressure value is obtained without winding the armband again. However, there is a problem that not only a structure of the armband is complicated but also a cost is increased and also and defective goods and failure are likely to be generated more often.

In the method (6), there is a problem that the estimated arm circumference length is largely changed according to strength of winding the armband.

SUMMARY OF THE INVENTION

Considering the aforementioned circumstances, an object of the present invention is to provide a noninvasive sphygmomanometer capable of obtaining an accurate blood pressure value without complicating a structure and with little time-consuming work.

A noninvasive sphygmomanometer according to a first embodiment of the invention comprises: a discharge amount measurer which measures a discharge amount of a pressure pump; and a measuring region circumference length calculator which calculates a measuring region circumference length of a subject person or a subject animal based on a relationship between a pressure in a gas bag provided in a measuring region enclosing portion which encloses a measuring region of the subject person or the subject animal and the discharge amount measured by the discharge amount measurer.

According to the invention according to the first embodiment, after the discharge amount of the pressure pump is measured by the discharge amount measurer, the measuring region circumference length is calculated by the measuring region circumference length calculator using the relationship between the discharge amount thereof and a change of the pressure in the gas bag. When the measuring region circumference length becomes long, an effective capacity of the gas bag becomes large according to the length that has become longer and the discharge amount until reaching a predetermined pressure is increased. Therefore, when the relationship between the discharge amount of the pressure pump and the pressure in the gas bag is calculated in advance, the measuring region circumference length can be easily estimated. Furthermore, if a wide range of the relationship between the discharge amount of the pressure pump and the pressure in the gas bag is calculated, such a work as a change of the measuring region enclosing portion according to the measuring region circumference length or the like becomes unnecessary or is decreased.

The noninvasive sphygmomanometer according to a second embodiment of the invention is, in the noninvasive sphygmomanometer according to the first embodiment of the invention, that the discharge amount measurer sets a first threshold value and a second threshold value higher than the first threshold value and less than or equal to a target pressure set value under measurement, and measures the discharge amount of the pressure pump until reaching the second threshold value from the first threshold value, using a pressure value in the gas bag after the gas bag expands with a gas discharged from the pressure pump and occupies a space between the measuring region and the measuring region enclosing portion.

According to the invention described in the second embodiment, the discharge amount measurer measures the discharge amount of the pressure pump between the two predetermined pressure values using the pressure values therebetween in the gas bag after the gas bag expands and occupies the space between the measuring region and the measuring region enclosing portion. In this case, even if the gas flows in the gas bag after the gas bag expands and occupies the space between the measuring region and the measuring region enclosing portion, a change of a capacity in the gas bag is inhibited by a region to be measured and the measuring region enclosing portion. Therefore, the pressure in the gas bag rises proportionally to the discharge amount of the pressure pump. Therefore, the accurate measuring region circumference length can be calculated if the discharge amount of the pressure pump is measured using the pressure values which are in the proportional relationship.

The noninvasive sphygmomanometer described in a third embodiment of the invention is, in the noninvasive sphygmomanometer according to the second embodiment of the invention, that a rotation number detector which counts the number of rotation of a motor for the pressure pump is provided on the pressure pump as the discharge amount measurer; and the number of rotation of the motor is counted and the discharge amount of the pressure pump is calculated by an output of the rotation number detector.

According to the invention described in third embodiment, the number of rotation of the motor for the pressure pump is counted by the output of the rotation number detector, and the discharge amount of the pressure pump is calculated according to the number of rotation thereof. A predetermined amount of the gas is exhausted from the pressure pump whose cylinder capacity is constant according to the number of rotation of the motor so that the accurate discharge amount of the pressure pump is calculated by counting the number of rotation thereof.

A noninvasive sphygmomanometer described in a fourth embodiment according to the invention comprises: a rotation number detector which counts the number of rotation of a motor for a pressure pump; and a measuring region circumference length calculator which calculates a measuring region circumference length of a subject person or a subject animal based on a relationship between a pressure in a gas bag provided in a measuring region enclosing portion which encloses a measuring region of the subject person or the subject animal and the number of rotation of the motor counted by the rotation number detector.

According to the invention described in the fourth embodiment, after the number of rotation of the motor in the pressure pump is counted by the rotation number detector, the measuring region circumference length is calculated by the measuring region circumference length calculator using the relationship between the number of rotation thereof and a change of the pressure in the gas bag. When the measuring region circumference length becomes long, an effective capacity of the gas bag becomes large according to the length that has become longer and the discharge amount until reaching a predetermined pressure is increased. In a type of the pressure pump which exhausts a predetermined amount of a gas according to the number of rotation of the motor from the cylinder in the pressure pump, if the relationship between the number of rotation thereof and the pressure in the gas bag is calculated in advance, the measuring region circumference length can be easily estimated.

The noninvasive sphygmomanometer described in a fifth embodiment according to the invention is, in the noninvasive sphygmomanometer according to the fourth embodiment, that the rotation number detector sets a first threshold value and a second threshold value higher than the first threshold value and less than or equal to a target pressure set value under measurement, and measures the number of rotation of the motor until reaching the second threshold value from the first threshold value, using a pressure value in the gas bag after the gas bag expands with a gas discharged from the pressure pump and occupies a space between the measuring region and the measuring region enclosing portion.

According to the invention described in fifth embodiment, the rotation number detector measures the number of rotation of the motor between the two predetermined pressure values using the pressure values therebetween in the gas bag after the gas bag expands and occupies the space between the measuring region and the measuring region enclosing portion. In this case, even if the gas flows in the gas bag after the gas bag expands and occupies the space between the measuring region and the measuring region enclosing portion, a change of a capacity in the gas bag is inhibited by a region to be measured and the measuring region enclosing portion. Therefore, the pressure in the gas bag rises proportionally to the number of rotation of the motor in the pressure pump whose cylinder capacity is constant. Therefore, the accurate measuring region circumference length can be calculated if the number of rotation of the motor is measured using the pressure values which are in the proportional relationship.

The noninvasive sphygmomanometer described in a sixth embodiment, in the noninvasive sphygmomanometer according to any one of the first through fifth embodiments, further comprises: a measurement result corrector which corrects a result of blood pressure measurement based on the measuring region circumference length of the subject person or the subject animal calculated by the measuring region circumference length calculator.

According to the invention described in the sixth embodiment, the result of the blood pressure measurement is corrected based on the measuring region circumference length of the subject person calculated by the measuring region circumference length calculator.

BRIEF DESCRIPTION OF THE DRAWINGS

FIG. 11 is a correction chart of Ragan & Bordley.

DETAILED DESCRIPTION OF THE PREFERRED EMBODIMENT(S)

Hereinafter, an embodiment of the present invention is explained with reference to the drawings.

Figure 1:
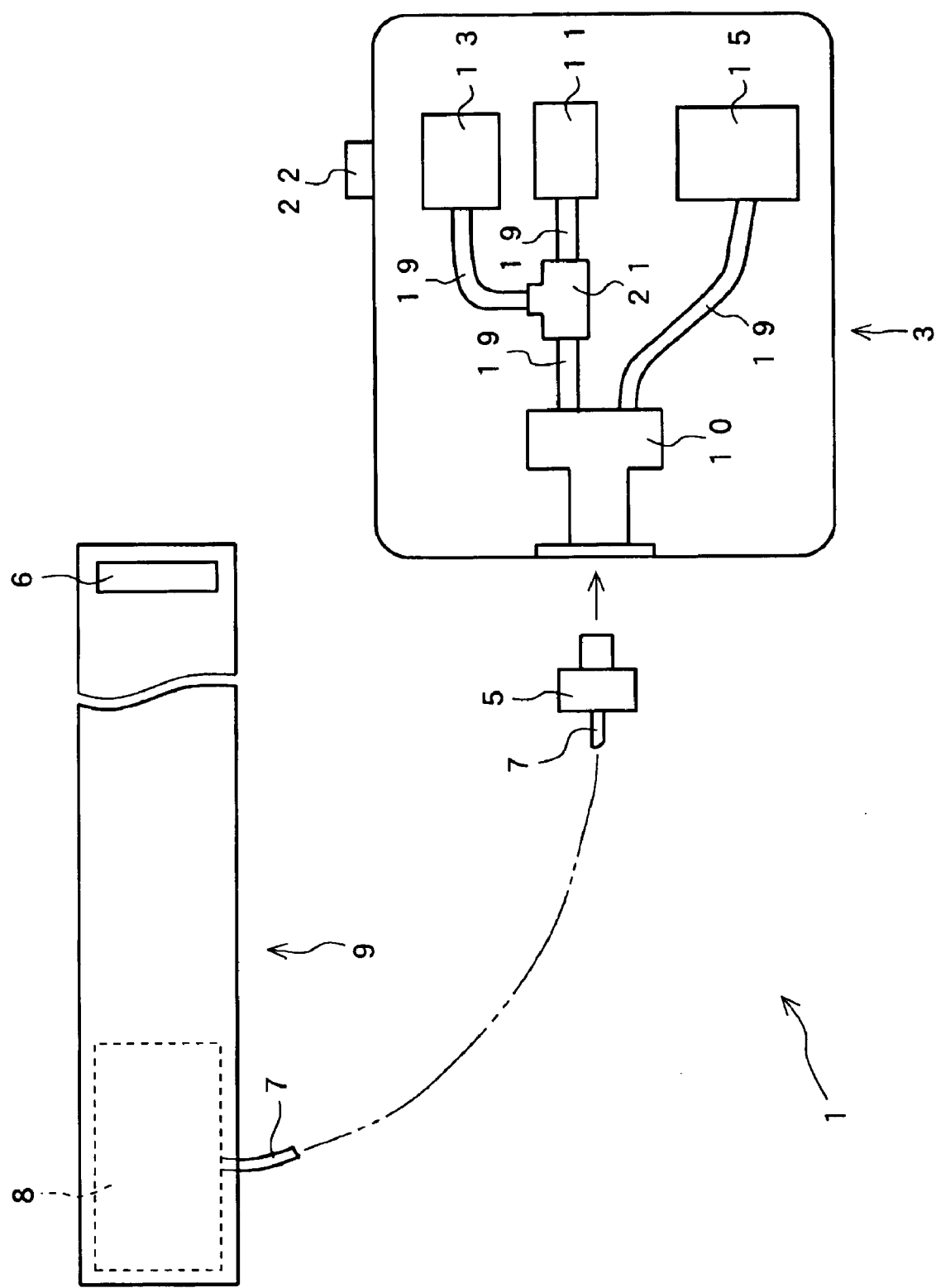
FIG. 1 is an explanatory view showing an embodiment of a noninvasive sphygmomanometer of the present invention.

FIG. 1 is an explanatory view showing an embodiment of a noninvasive sphygmomanometer of the present invention. A noninvasive sphygmomanometer 1 includes a sphygmomanometer body 3 and an armband 9 as a measuring region enclosing portion which encloses the measuring region of a subject person. A bladder 8 as a gas bag to which an air is sent from the sphygmomanometer body 3 through a plug 5 and a tube 7 is provided in the armband 9. Furthermore, on the armband 9, a Velcro (trademark) 6 for not shrinking after winding the armband 9 on an arm of the subject person is provided.

The sphygmomanometer body 3 includes a connector 10 which plugs the plug 5, a slow leakage valve 11 which adjusts a slow leak rate under blood pressure measurement, and a pressure pump 13 which sends the air to the bladder 8. Furthermore, the sphygmomanometer body 3 includes a pressure sensor 15 which measures a pressure in the bladder 8, tubes 19 and a joint 21 which link the aforementioned various components. Furthermore, the sphygmomanometer body 3 has a power supply switch 22 on an outside face thereof.

Figure 2:
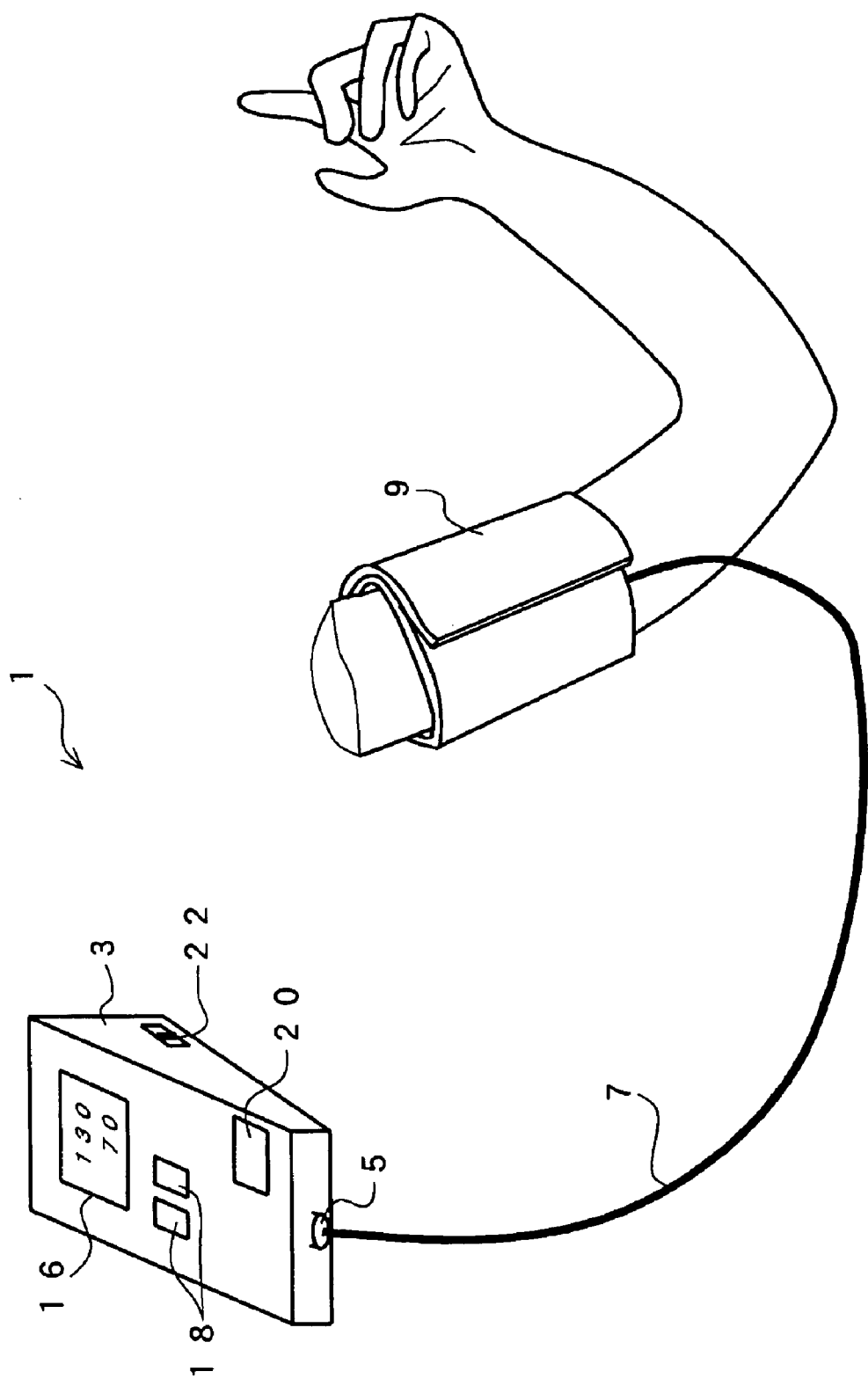
FIG. 2 is an explanatory view showing a method for using the noninvasive sphygmomanometer in FIG. 1.

Subsequently, a method for using the noninvasive sphygmomanometer 1 will be explained using FIG. 2. First, the power supply switch 22 of the sphygmomanometer body 3 is turned on. Next, the subject person relaxes his/her arm, and the subject person him/herself or a measuring person other than the subject person winds the armband 9 on an upper arm of the subject person. Next, a maximum pressure value for applying to the bladder 8 is determined according to an approximate maximum blood pressure value of the subject person by an operation button 18. When a start button 20 is pressed, the air flows in the bladder 8 from the sphygmomanometer body 3 through the tube 7, thereby blood pressure measurement starts. It should be noted that a pressure change in the bladder 8 under measurement, a maximum blood pressure value and a minimum blood pressure value as measurement results, or the like are displayed on a monitor 16. Furthermore, it may be appropriate if a pulse or the like is displayed thereon after completing the blood pressure measurement.

Subsequently, the pressure pump 13 will be explained in detail using FIG. 3. The pressure pump 13 includes a motor 23 as a driving source for discharging the air. Two electrodes 23a are provided at a rear end side of the motor 23, and the motor 23 is activated by applying a voltage of, for example, DC 6V to these two electrodes 23a. Furthermore, a rotating shaft 23b is projecting at a front end side of the motor 23, and the rotating shaft 23b is pressed into a rotor 25 made of resin on which a fitting hole 25a is formed at a center. Furthermore, on the rotor 25, a fitting hole 25b is formed on a side opposite to an opening side of the fitting hole 25a. The fitting hole 25b is formed by deviating from a center axis Z. Furthermore, a thin fan-shaped shielding plate 25c is provided on an outer periphery of the rotor 25, and is integrally formed with a rotor body 25d.

On one side of the rotor 25, a cup-shaped cylindrical portion 27 on which a through hole 27a where the rotor 25 is insertable is formed is provided. The cylindrical portion 27 is fixed to the motor 23 in such a manner that screws 29 are respectively inserted in two through holes 27d (disposed in a vertical direction in the drawing) formed through a bottom portion 27e, and are screwed together in female screws 23c formed on the motor 23. Furthermore, in the cylindrical portion 27, a photointerrupter 31 as a component of a rotation number detector which counts the number of rotation of the motor 23 is provided.

The photointerrupter 31 is so structured that a photocoupler 31b having a recess-shaped cross section is soldered and fixed on an electrode substrate 31a. In the photocoupler 31b, a light emitting diode 33 and an npn phototransistor 35 shown in an electric circuit 55 in FIG. 6 to be described later are provided, and a light passes from one side to the other of a recessed groove. Every time the motor 23 makes one rotation, the shielding plate 25c formed on the rotor 25 passes through the recessed groove and shields the light of the light emitting diode 33; thereby the number of rotation of the motor 23 is counted. Incidentally, a harness 37 is connected to the electrode substrate 31a.

On one side of the cylindrical portion 27, a cylinder-biasing portion 38 is provided. The cylinder-biasing portion 38 includes an axle 41 made of metal to be fitted into the fitting hole 25b, a cylindrical portion 43a made of resin where the axle 41 is pressed, and a cylinder-biasing portion 43 having gin plate portions 43b integrally formed with the cylindrical portion 43a. Rubber cylinder-biasing projecting portion 45 are provided on the respective gin plate portions 43b, and a rubber cylinder 40 provided in a cylinder portion 39 is biased and transformed by the cylinder-biasing projecting portions 45.

On one side of a cylinder portion 39, a nozzle portion 49 is provided. On the nozzle portion 49, a spouting hole 49a is provided. When the rubber cylinder 40 is transformed, the air in the cylinder 40 is pushed out and passed through the spouting hole 49a. The transformation of the cylinder 40 is carried out by an eccentric motion of the cylinder-biasing portion 43 and by biasing the rubber cylinder 40 toward one side because the axle 41 is pressed into the fitting hole 25b formed by deviating from the center axis Z.

Figure 3:
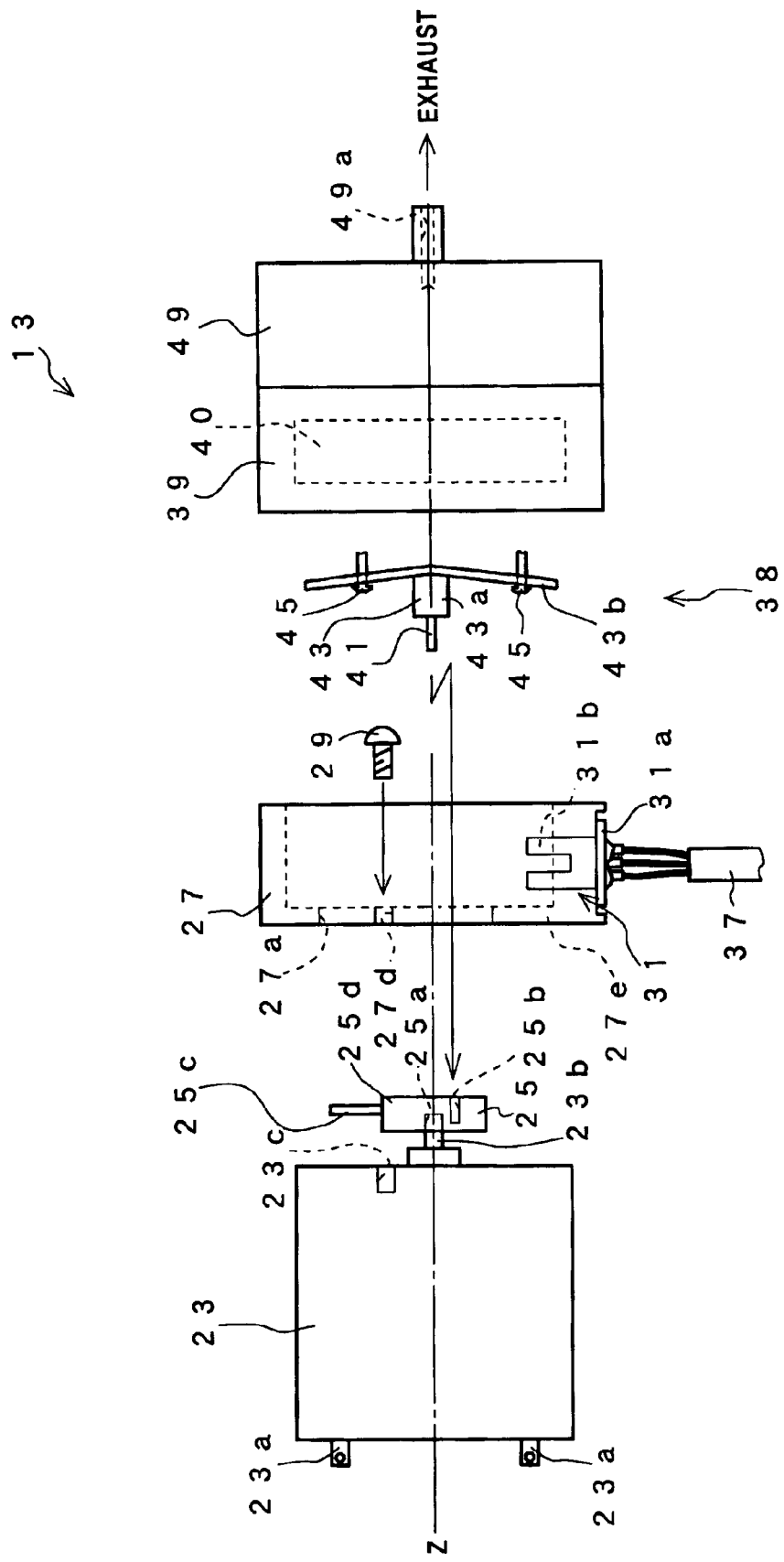
FIG. 3 is an exploded view showing details of a pressure pump in FIG. 1.
Figure 4:
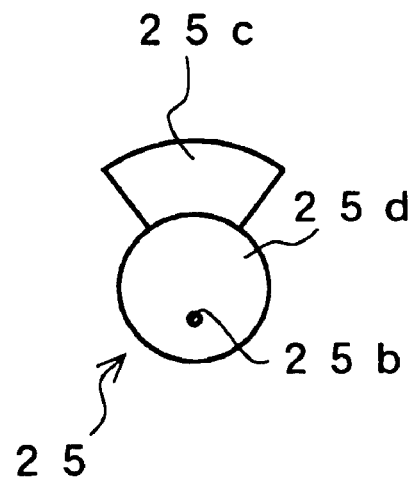
FIG. 4 is an explanatory view showing a rotor in FIG. 3.

FIG. 4 is a front view when the rotor 25 in FIG. 3 is seen from one side. As explained above, the fitting hole 25b is formed on a position different from a center of the rotor body 25d. The fan-shaped shielding plate 25c is formed on the outer periphery of the rotor body 25d away from the fitting hole 25b.

Figure 5:
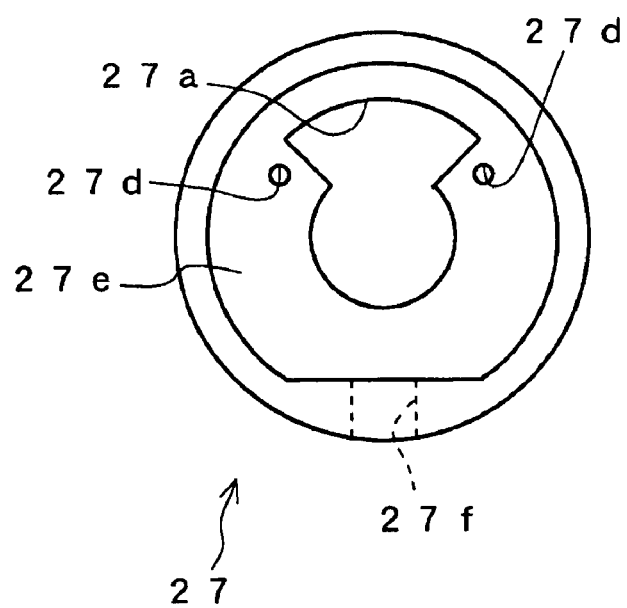
FIG. 5 is an explanatory view showing a first cylindrical portion in FIG. 3.

FIG. 5 is a front view when the cylindrical portion 27 in FIG. 3 is seen from one side. The through hole 27a having the same shape as a shape of the rotor 25 seen from the front is formed on the bottom portion 27e of the cup-shaped cylindrical portion 27, and the rotor 25 is insertable therein. Furthermore, the through holes 27d are respectively formed on both sides of the through holes 27a, and a through hole 27f for inserting the photocoupler 31b of the phottointerrupter 31 is formed on a bottom side thereof.

Figure 6:
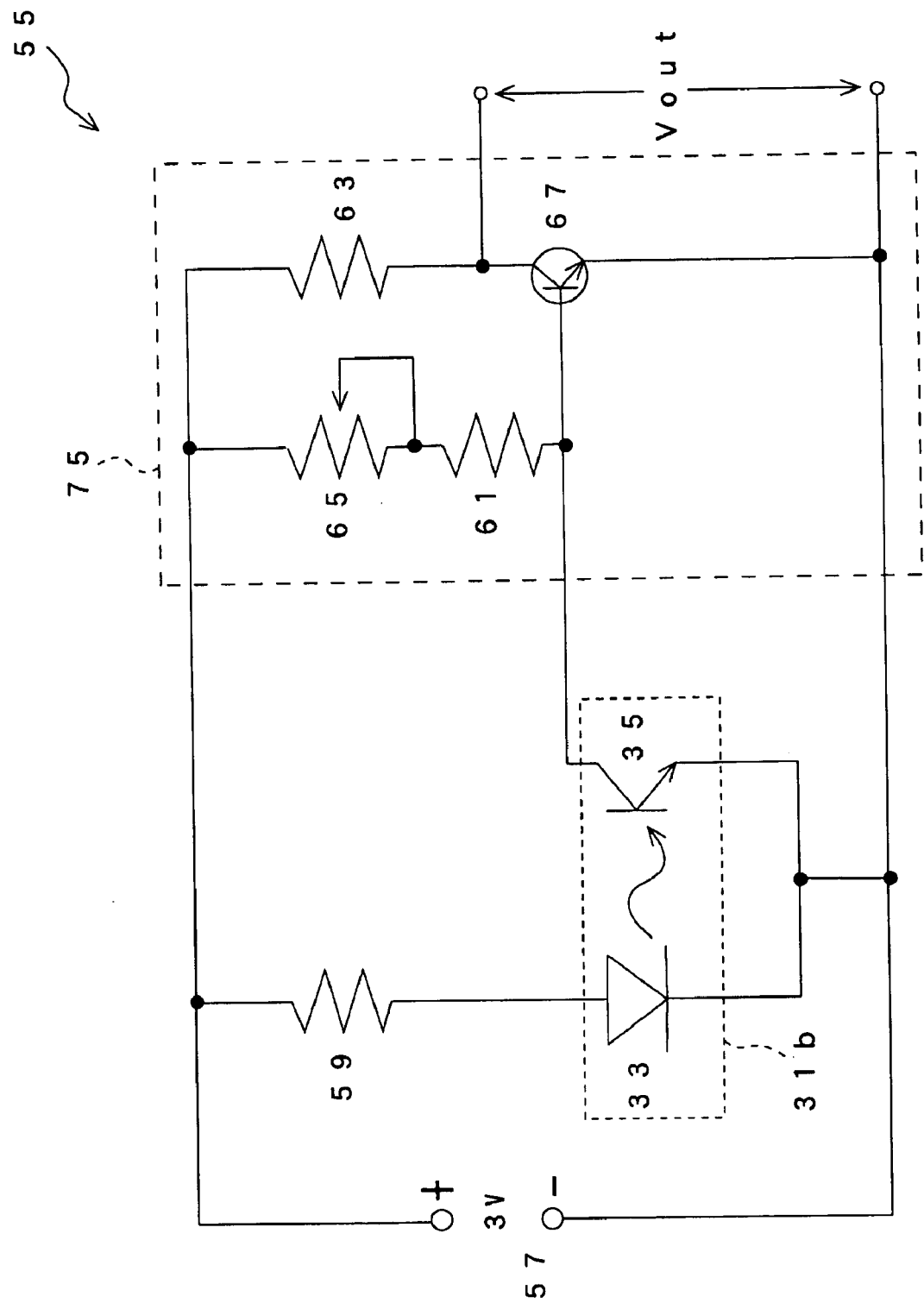
FIG. 6 is an electric circuit diagram including a photocoupler in FIG. 3.

FIG. 6 is an electric circuit diagram including the photocoupler 31b. The electric circuit 55 includes a power supply 57, resistors 59, 61, 63, and a variable resistor 65. DC 3V is used for the power supply 57. Furthermore, the light emitting diode 33 is connected to the resistor 59, and the phototransistor 35 is connected to the resistor 61. A collector of an npn transistor 67 is connected to the resistor 63, and a base of the npn transistor 67 is connected to the resistor 61. Furthermore, a wave-shaping circuit 75 which outputs rectangular waves is formed by the resistors 61, 63, the variable resistor 65, and the npn transistor 67.

The electric circuit 55 is so structured that an electric current flows in the light emitting diode 33 through the resistor 59 and the light emitting diode 33 is lighted when an electric power is supplied from the power supply 57. Here, when the shielding plate 25c mounted on the rotor 25 does not shield between the light emitting diode 33 and the phototransistor 35, a light energy emitted from the light emitting diode 33 is supplied to a base of the phototransistor 35, and therefore, a state between a collector and an emitter of the phototransistor 35 is in an on state so that the electric current is not supplied to the base of the npn transistor 67. Accordingly, a state between the collector and an emitter of the npn transistor 67 is in an off state, and an output voltage Vout is 3V which is an approximate power supply voltage.

However, when the motor 23 rotates and when the shielding plate 25c of the rotor 25 comes to a position to shield the light between the light emitting diode 33 and the phototransistor 35, the light energy from the light emitting diode 33 supplied to the base of the phototransistor 35 is shielded, and therefore, a state between the collector and the emitter of the phototransistor 35 is in an off state. As a result, the electric current is supplied to the base of the npn transistor 67 through the variable resistor 65 and the resistor 61, and a state between the collector and the emitter of the npn transistor 67 is in an on state so that the output voltage Vout is almost 0V.

Accordingly, the output voltage Vout synchronizes the rotation of the motor 23 and alternately repeats 0V and 3V.

Therefore, by counting the number of changes of the voltage Vout, the number that the shielding plate 25c shields the light from the light emitting diode 33 to the phototransistor 35 can be counted, thereby the number of rotation of the motor 23 can be counted.

It should be noted that the variable resistor 65 is a resistor which adjusts scattering of amplification of the phototransistor 35.

Figure 7:
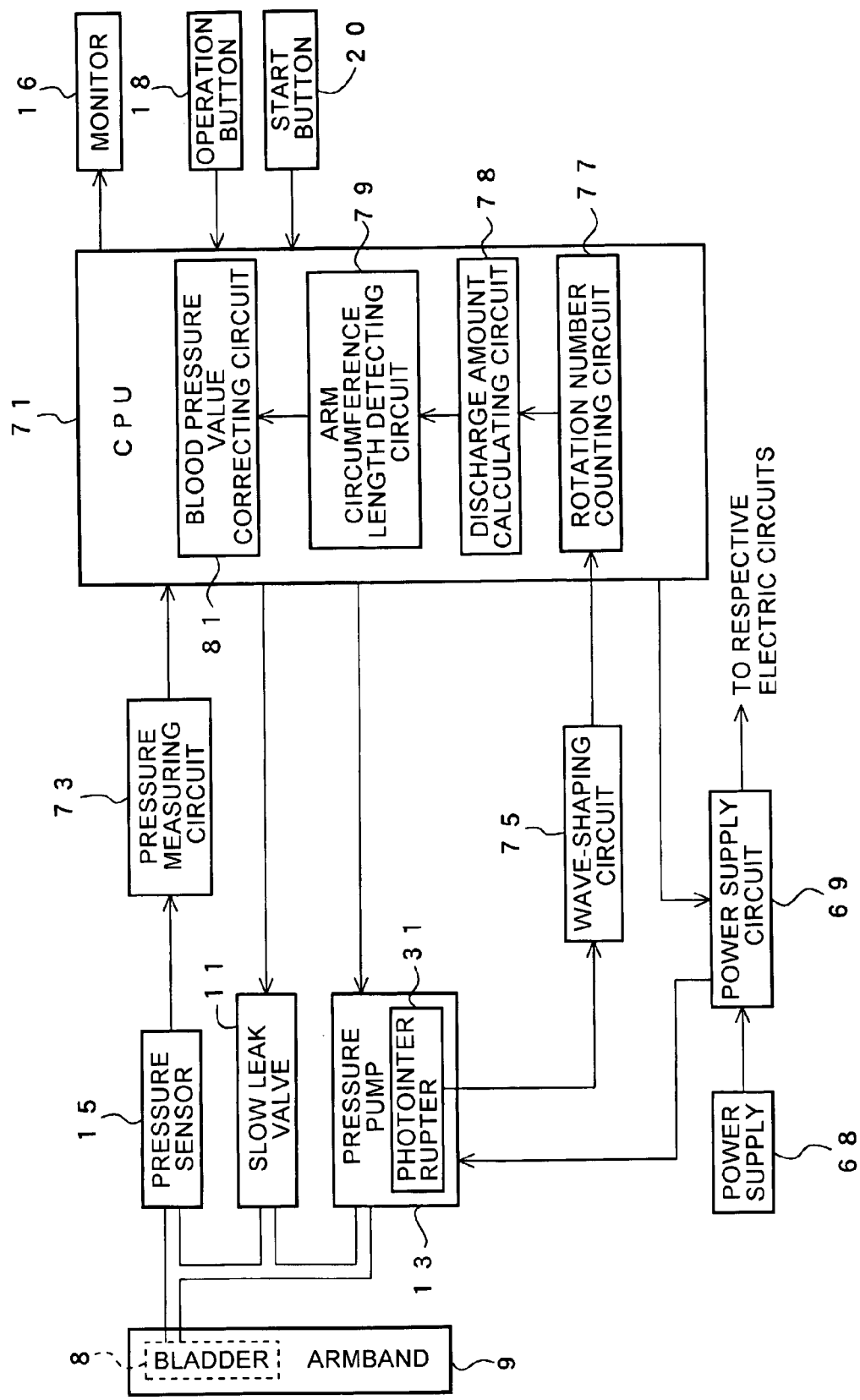
FIG. 7 is a block diagram of the noninvasive sphygmomanometer in FIG. 1.

FIG. 7 is a block diagram of the noninvasive sphygmomanometer 1. A process for calculating blood pressure will be explained using the block diagram thereof. First, when the power supply switch 22 (described in FIG. 1) is turned on, an electric power is supplied from a power supply 68 to a power supply circuit 69. Then, the electric power is supplied from the power supply circuit 69 to respective electric circuits, the pressure pump 13, and the like. Subsequently, as explained using FIG. 2, the armband 9 is wound on the upper arm of the subject person, and the start button 20 is pressed after setting conditions of the blood pressure measurement by the operation button 18.

Then, the pressure pump 13 is activated by a signal from a CPU 71 and the air is sent to the bladder 8 provided in the armband 9. When the pressure in the bladder 8 rises to a set value, the slow leak valve 11 is half open, the air in the bladder 8 is released to atmosphere little by little, and the pressure therein is gradually decreased at a predetermined speed. The pressure in the bladder 8 is observed by the pressure sensor 15, and pulses whose frequency is changed according to the observed pressure value are outputted. The pulses are converted to the pressure value by a pressure measuring circuit 73, and are displayed in real time by the monitor 16 at every predetermined time. It should be noted that the slow leak valve 11 is fully open after completing the blood pressure measurement and rapidly decreases the pressure in the bladder 8.

Furthermore, a waveform of the output voltage Vout of the electric circuit 55 (described in FIG. 6) including the photointerrupter 31 and the wave-shaping circuit 75 is inputted to a rotation number counting circuit 77 as an internal circuit of the CPU 71. Then, by the rotation number counting circuit 77, the number of the rectangular waves from the wave-shaping circuit 75 is counted while the pressure in the bladder 8 reaches a first threshold value and decreases to a second threshold value. Here, the first threshold value is considered as a value after the bladder 8 expands and occupies a space between the upper arm and the armband 9. In other words, the pressure in a state that a change of the pressure measured by the pressure sensor 15 has a proportional relationship with a discharge amount of the pressure pump 13 is adopted as the first threshold value. For example, the value can be set as 40 mmHg. On the other hand, the second threshold value is considered as a value higher than the first threshold value and less than or equal to a target pressure set value under measurement. For example, the value can be set as 160 mmHg. The target pressure set value under measurement is set, for example, 30 to 40 mmHg higher than an estimated maximum blood pressure value of the subject person.

It should be noted that a rotation number detector includes the photointerrupter 31, the wave-shaping circuit 75, and the rotation number counting circuit 77.

Subsequently, a discharge amount is calculated by a discharge amount calculating circuit 78 based on count numbers of the rectangular waves by the rotation number counting circuit 77, which means the number of rotation of the motor 23 (described in FIG. 3). It should be noted that a discharge amount calculator is constituted by the discharge amount calculating circuit 78 and the aforementioned rotation number detector.

Figure 8:
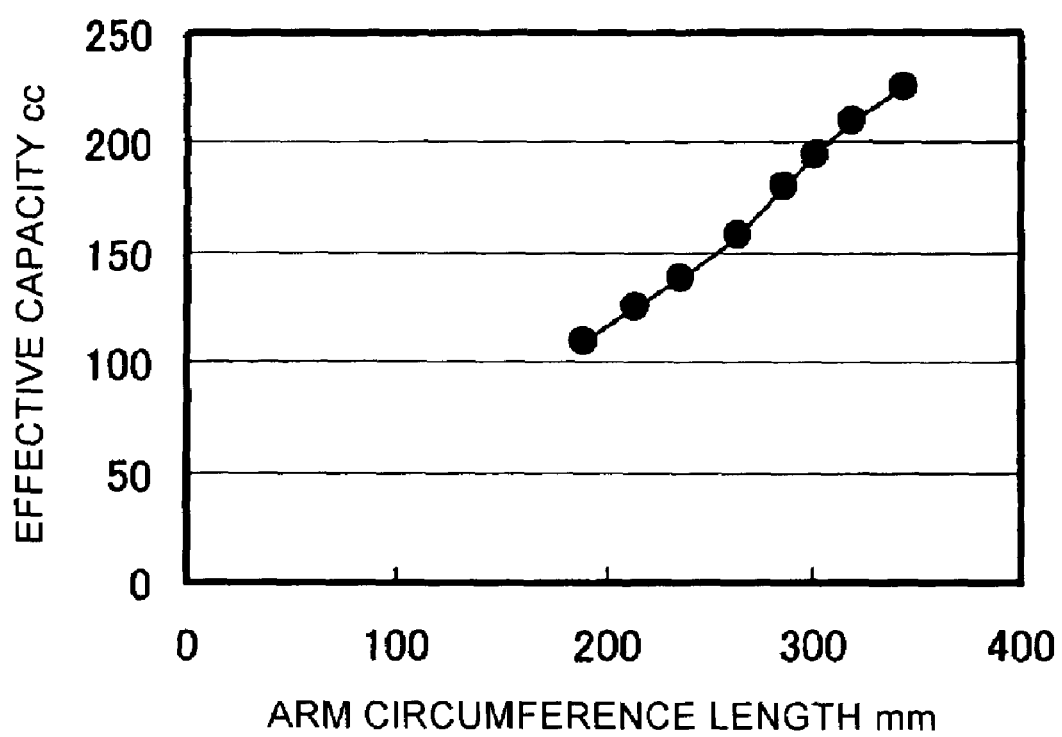
FIG. 8 is a graph showing a relationship between an effective capacity of a bladder and an arm circumference length.
Figure 9:
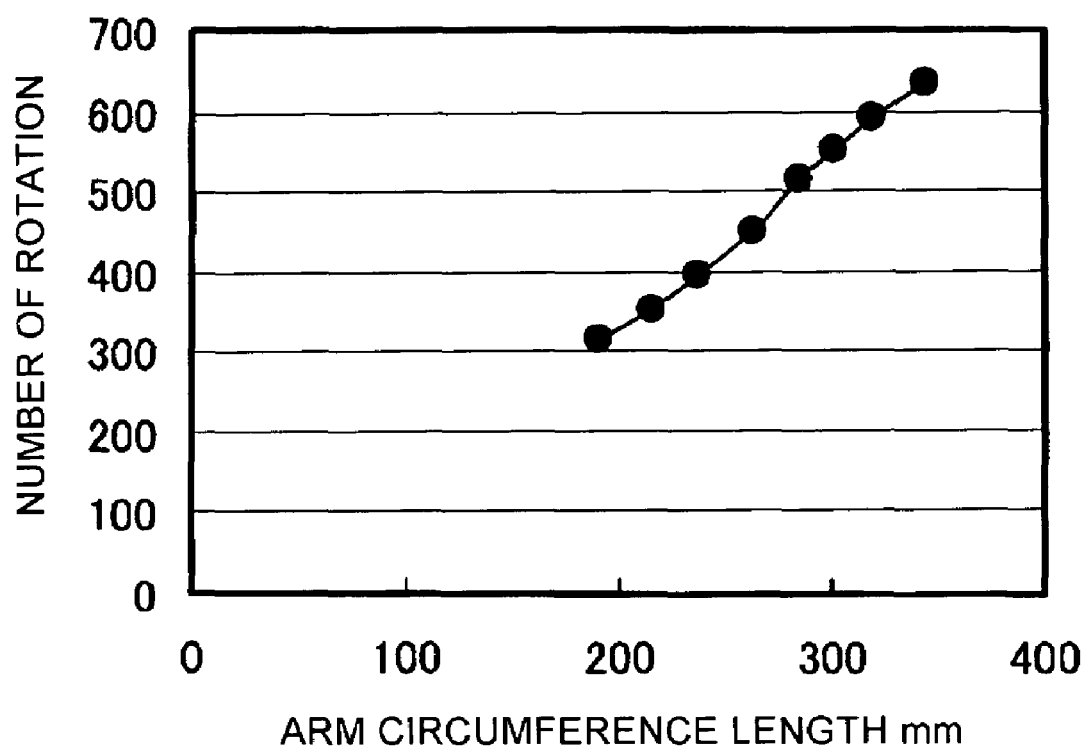
FIG. 9 is a graph showing a relationship between the number of rotation of a motor and the arm circumference length.

Subsequently, an arm circumference length is calculated by an arm circumference length detecting circuit 79 as a measuring region circumference length detector based on the discharge amount calculated by the discharge amount calculating circuit 78 while the pressure in the bladder 8 reaches the second threshold value from the first threshold value. The reason why the arm circumference length is thus estimated is that, the longer the arm circumference length is, the larger the effective capacity in the bladder 8 is and the more the amount of the air requiring for increasing by a predetermined pressure is increased. FIG. 8 shows a relationship between the effective capacity of the bladder 8 and the arm circumference length. As can be seen in the drawing, the arm circumference length is measured between 190 mm and 345 mm, and the effective capacity of the bladder 8 becomes large substantially proportionally to the arm circumference length when it becomes large. FIG. 9 shows a relationship between the number of rotation of the motor 23 and the arm circumference length. Since an amount that the air of the motor 23 is exhausted per rotation is constant, FIG. 9 is a similar graph to FIG. 8.

Figure 10:
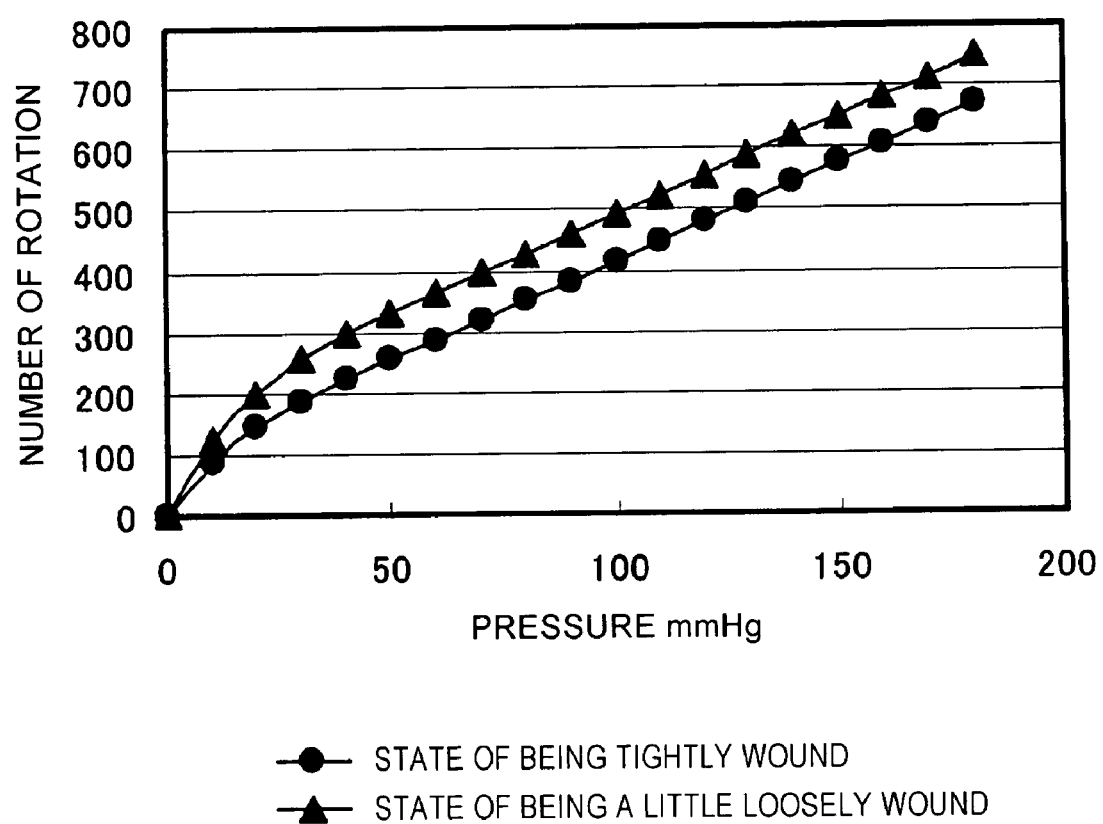
FIG. 10 is a graph showing a comparison between when an armband in FIG. 1 is tightly wound and when the armband is a little loosely wound.

FIG. 10 shows a relationship between the number of rotation of the motor 23 and the pressure in the bladder 8 according to a difference in winding of the armband 9. The drawing is a graph showing when the armband 9 is wound on the arm of a subject person having an arm circumference length of 260 mm and when the pressure is applied to 180 mmHg. A line with black circle dots is a line showing when the armband 9 is tightly wound on the arm of the subject person, which means winding under general measurement. On the other hand, a line with black triangle dots is a line showing when the armband 9 is a little loosely wound. As can been seen in the drawing, the loosely wound armband 9 shows more number of rotation of accumulation until reaching the same pressure than the tightly wound armband 9 because the loosely wound armband 9 has more of the effective capacity in the bladder 8.

However, slopes of both graphs have such a common point that they are substantially linear after approximately 40 mmHg. This means that the bladder 8 occupies the space between the measuring region and the armband 9 when the pressure in the bladder 8 is approximately 40 mmHg. Therefore, the arm circumference length can be estimated with high accuracy when the first threshold value and the second threshold value are adopted on two points with a wide range of the straight line.

Subsequently, a result of the blood pressure measurement is corrected by a blood pressure value correcting circuit 81 as a measurement result corrector based on the arm circumference length of the subject person calculated by the arm circumference length detecting circuit 79. Specifically, a correction table by Ragan & Bordley, a correction formula by Pickering, or the like is applied as shown in FIG. 11. Incidentally, the correction formula by Pickering is as follows:

$$s=1.27c-35.86; d=0.87c-15.54$$

s: maximum blood pressure value (mmHg) c: upper arm circumference length (mm) d: minimum arm circumference value (mmHg).

Furthermore, a table in FIG. 11 shows a rate of change of a maximum blood pressure value and a minimum blood pressure value according to an upper arm circumference length when the bladder 8 of 13 cm wide is used. For example, for a subject person having an upper arm circumference length of 240 mm, such corrections are made that 5 mmHg is added to the measured maximum blood pressure value, and that 5 mmHg is subtracted from the minimum blood pressure value.

Finally, the corrected maximum blood pressure value and minimum blood pressure value are displayed on the monitor 16 and the measurement is completed.

According to an embodiment of the present invention as mentioned above, after the discharge amount of the pressure pump 13 is measured by detecting the number of rotation of the motor 23 by the photointerrupter 31, the arm circumference length is calculated by the arm circumference length detecting circuit 79 using the relationship between the discharge amount thereof and a change of the pressure in the bladder 8. When the arm circumference length becomes long, the effective capacity of the bladder 8 becomes large according to the length that has become longer and the discharge amount until reaching a predetermined pressure is increased. Therefore, when the relationship between the discharge amount of the pressure pump 13 and the pressure in the bladder 8 is calculated in advance, the arm circumference length can be easily estimated. Accordingly, the present invention can be realized by a simple design change of only providing the photointerrupter 31 in the pressure pump 13 and of further providing the electric circuit such as the wave-shaping circuit 75, the rotation number counting circuit 77, and the like, and therefore, the arm circumference length can be estimated without complicating its structure. Furthermore, an accurate blood pressure value can be obtained if the blood pressure value is corrected by the blood pressure value correcting circuit 81 based on the arm circumference length. Furthermore, if a wide range of the relationship between the discharge amount of the pressure pump 13 and the pressure in the bladder 8 is calculated, the blood pressure measurement with little time-consuming work can be carried out because such a work as a change of the armband 9 according to the arm circumference length or the like is decreased.

Furthermore, an output of the photointerrupter 31 is inputted to the blood pressure value correcting circuit 81 via the wave-shaping circuit 75, the rotation number counting circuit 77, the discharge amount calculating circuit 78, and the arm circumference length detecting circuit 79, thereby the blood pressure measurement can be automatically carried out. Therefore, there is no need to directly input the measured arm circumference length to the noninvasive sphygmomanometer 1, and the rapid blood pressure measurement can be carried out with little time-consuming work.

Furthermore, when the discharge amount is calculated by the number of rotation of the motor 23, the accurate discharge amount can be calculated because the capacity of the cylinder 40 is constant. Conventionally, the discharge amount is calculated using a time of rotation of the motor 23; therefore, an error of an output change due to aging of a battery is generated, or a load is changed due to a change of the pressure in the bladder 8 even if an output of the battery is constant, resulting in a generation of an error. However, these problems can be solved.

Furthermore, according to an embodiment of the present invention, the discharge amount of the pressure pump 13 between the two pressure values is measured using the two pressure values in the bladder 8 after the bladder 8 expands and occupies the space between the arm and the armband 9; in this case, even if the air flows in the bladder 8 after the bladder 8 expands and occupies the space between the arm and the armband 9, a change of the capacity in the bladder 8 is inhibited by the arm and the armband 9. Furthermore, the pressure in the bladder 8 rises proportionally to the discharge amount of the pressure pump 13. Therefore, the accurate arm circumference length can be calculated using the pressure values which are in the proportional relationship. Therefore, a generation of the error of the measurement result due to loosely winding the armband 9 can be prevented.

Incidentally, in an embodiment explained above, an example of winding the armband 9 on the upper arm of the subject person as a measuring region is given; however, the present invention is not limited to the above. For example, the armband 9 can be wound on a wrist, a leg, or other regions.

Furthermore, in an embodiment explained above, an example of winding the armband 9 to the subject person as a target is given; however, the target may be an animal.

Furthermore, in an embodiment explained above, an example of sending air to the bladder 8 as a gas is given; however, other gas may be acceptable.

Furthermore, in an embodiment explained above, an example of calculating the discharge amount by the discharge amount calculating circuit 78 and of estimating the arm circumference length by the arm circumference length detecting circuit 79 after counting the number of rotation of the motor 23 by the rotation number counting circuit 77 is given; however, the relationship between the number of rotation of the motor 23 between the two pressure values and the arm circumference length can be calculated in advance and the arm circumference length can be estimated without calculating the discharge amount.

As explained above, according to the present invention, after the discharge amount of the pressure pump is measured, the arm circumference length is calculated by a measuring region circumference length calculator using the relationship between the discharge amount thereof and the change of the pressure in the gas bag. When the arm circumference length becomes long, the effective capacity of the gas bag becomes large according to the length that has become longer and the discharge amount until reaching a predetermined pressure is increased. Therefore, when the relationship between the discharge amount of the pressure pump and the pressure in the gas bag is calculated in advance, the measuring region circumference length can be easily estimated. Accordingly, the present invention can be realized by a simple design change, for example, if the rotation number detector is provided with the pressure pump and if the discharge amount is measured; therefore, the arm circumference length can be estimated without complicating the structure. Furthermore, the accurate blood pressure value can be obtained if the blood pressure value is corrected by the measurement result corrector based on the arm circumference length. Furthermore, if a wide range of the relationship between the discharge amount of the pressure pump and the pressure in the gas bag is calculated, such a work as attachment or detachment of the measuring region enclosing portion according to the measuring region circumference length or the like is decreased, thereby the accurate blood pressure value can be obtained with little time-consuming work.

What is claimed is:

1. A noninvasive sphygmomanometer, comprising:
a discharge amount measurer which measures a discharge amount of a pressure pump; and
a measuring region circumference length calculator which calculates a measuring region circumference length of a subject person or a subject animal based on a relationship between a pressure in a gas bag provided in a measuring region enclosing portion which encloses a measuring region of the subject person or the subject animal and the discharge amount measured by said discharge amount measurer wherein
said discharge amount measurer sets a first threshold value and a second threshold value higher than the first threshold value and less than or equal to a target pressure set value under measurement, and measures the discharge amount of the pressure pump until reaching the second threshold value from the first threshold value, using a pressure value in the gas bag after the gas bag expands with a gas discharged from the pressure pump and occupies a space between the measuring region and the measuring region enclosing portion.

2. The noninvasive sphygmomanometer according to claim 1, wherein
a rotation number detector which counts the number of rotation of a motor for the pressure pump is provided on the pressure pump as said discharge amount measurer; and
the number of rotation of the motor is counted and the discharge amount of the pressure pump is calculated by an output of the rotation number detector.

3. A noninvasive sphygmomanometer comprising:
a rotation number detector which counts the number of rotation of a motor for a pressure pump: and
a measuring region circumference length calculator which calculates a measuring region circumference length of a subject person or a subject animal based on a relationship between a pressure in a gas bag provided in a measuring region enclosing portion which encloses a measuring region of the subject person or the subject animal and the number of rotation of the motor counted by said rotation number detector wherein
said rotation number detector sets a first threshold value and a second threshold value higher than the first threshold value and less than or equal to a target pressure set value under measurement, and measures the number of rotation of the motor until reaching the second threshold value from the first threshold value, using a pressure value in the gas bag after the gas bag expands with a gas discharged from the pressure pump and occupies a space between the measuring region and the measuring region enclosing portion.

* * * * *